United States Patent
Perlman et al.

(10) Patent No.: US 7,196,619 B2
(45) Date of Patent: *Mar. 27, 2007

(54) HABIT CESSATION AIDE

(76) Inventors: Neil Perlman, 35 Coldstream Cir., Lincolnshire, IL (US) 60069; Daniel Mapes-Riordan, 1433 Judson Ave., Evanston, IL (US) 60201

( * ) Notice: Subject to any disclaimer, the term of this patent is extended or adjusted under 35 U.S.C. 154(b) by 0 days.

This patent is subject to a terminal disclaimer.

(21) Appl. No.: 10/186,903

(22) Filed: Jun. 29, 2002

(65) Prior Publication Data

US 2004/0001001 A1    Jan. 1, 2004

(51) Int. Cl.
*B60Q 1/00*    (2006.01)
(52) U.S. Cl. .............. 340/457; 340/309.7; 340/309.16; 340/573.1; 131/270; 434/238; 368/109
(58) Field of Classification Search ................ 340/457, 340/309.7, 309.8, 573.1, 309.4, 309.15, 309.16; 434/236, 238, 127; 131/270; 368/107, 108, 368/1, 10, 281, 109

See application file for complete search history.

(56) References Cited

U.S. PATENT DOCUMENTS

| | | | |
|---|---|---|---|
| 4,630,935 A | 12/1986 | Zettek | |
| 4,853,854 A | 8/1989 | Behar et al. | |
| 4,965,553 A * | 10/1990 | DelBiondo, II et al. | . 340/573.1 |
| 5,285,430 A | 2/1994 | Decker | |
| 5,813,026 A | 9/1998 | Borg | |
| 5,833,466 A * | 11/1998 | Borg | 434/236 |
| 5,861,797 A | 1/1999 | Becker | |
| 5,908,301 A * | 6/1999 | Lutz | 434/236 |
| 6,305,839 B1 * | 10/2001 | Krstulovic | 368/281 |
| 6,448,887 B1 * | 9/2002 | Martin et al. | 340/309.4 |
| 6,473,368 B1 * | 10/2002 | Stanfield | 368/107 |
| 6,839,305 B2 | 1/2005 | Perlman et al. | |

* cited by examiner

*Primary Examiner*—Davetta W. Goins

(57) ABSTRACT

A habit cessation aide includes a user-modifiable quitting schedule, a user-initiated habit-occurrence indicator, a display for displaying messages dependent upon the quitting schedule and the number of times the user-initiated habit-occurrence indicator is used, and an overall visual indication of the degree to which the user is maintaining the quitting schedule based upon the quitting schedule and the number of times the user-initiated habit-occurrence indicator is used. A widely held habit is smoking, to which the illustrated embodiment is directed. As shown, the device also functions as a standard watch and includes features such as calculating and displaying items including at least time, date, and elapsed time.

6 Claims, 3 Drawing Sheets

HABIT CESSATION AIDE

BACKGROUND OF THE INVENTION

This device relates to habit devices generally, and more particularly to a habit cessation aide, such as a smoking cessation aide.

Approximately 25% of the American population currently smokes. Smoking contributes to numerous medical problems and an early death in approximately one-third of smokers. Because smoking is very addictive, most smoking cessation methods have poor success rates. Studies have shown that nicotine patches, gum and sprays have a 25%–58% short-term success rate and only a 11%–28% one year success rate. According to published studies, the anti-smoking prescription medication Bupropion (Zyban) has a 55% success rate when combined with smoking cessation therapy, and 20% short-term success rate without therapy. Various other methods, including medications, acupuncture, hypnosis, counseling, ear bands, etc., have also been utilized without substantial success. A principal reason for the low success rates is that people wanting to quit smoking often need regular positive and negative reinforcement that the above methods and devices cannot provide.

Other habits may be broken with the advantage of regular reinforcement.

SUMMARY OF THE INVENTION

A primary object of the present invention is to provide reinforcement to help a smoker quit smoking.

A related object of the present invention is to provide periodic and on-demand reinforcement to help users with a repetitive habit quit that habit.

In accordance with a preferred embodiment of the present invention a habit cessation aide comprises a user-modifiable quitting schedule, a user-initiated habit-occurrence indicator, a display for displaying messages dependent upon the quitting schedule and the number of times the user-initiated habit-occurrence indicator is used, and an overall visual indication of the degree to which the user is maintaining the quitting schedule based upon the quitting schedule and the number of times the user-initiated habit-occurrence indicator is used.

In the preferred embodiment, the habit is smoking. The smoking cessation aide of the preferred embodiment of the present invention appears similar to a standard watch but may also be in the form of a key chain fob. Besides having a standard display and side buttons, it has 'cigarette' and 'information' buttons on the face. The cigarette button and the programming inside the watch track cigarette smoking. The user is simply required to tap the cigarette button at the onset of starting each tobacco product. By utilizing positive and negative feedback, the user is encouraged to diminish and eventually quit the tobacco habit. The cessation aide utilizes various displays, messages, auditory and vibratory alarms to provide feedback.

Other objects and advantages of the habit cessation aide will become apparent from the following descriptions, taken in connection with the accompanying drawings, wherein, by way of illustration and example, an embodiment of the present invention is disclosed.

BRIEF DESCRIPTION OF THE SEVERAL VIEWS OF THE DRAWINGS

The drawings constitute a part of this specification and include exemplary embodiments to the invention, which may be embodied in various forms. It is to be understood that in some instances various aspects of the invention may be shown exaggerated or enlarged to facilitate an understanding of the invention.

DETAILED DESCRIPTION OF THE PREFERRED EMBODIMENTS

Detailed descriptions of the preferred embodiment are provided herein. It is to be understood, however, that the present invention may be embodied in various forms. Various aspects of the invention may be inverted, or changed in reference to specific part shape and detail, part location, or part composition. Therefore, specific details disclosed herein are not to be interpreted as limiting, but rather as a basis for the claims and as a representative basis for teaching one skilled in the art to employ the present invention in virtually any appropriately detailed system, structure or manner.

Figure 1:
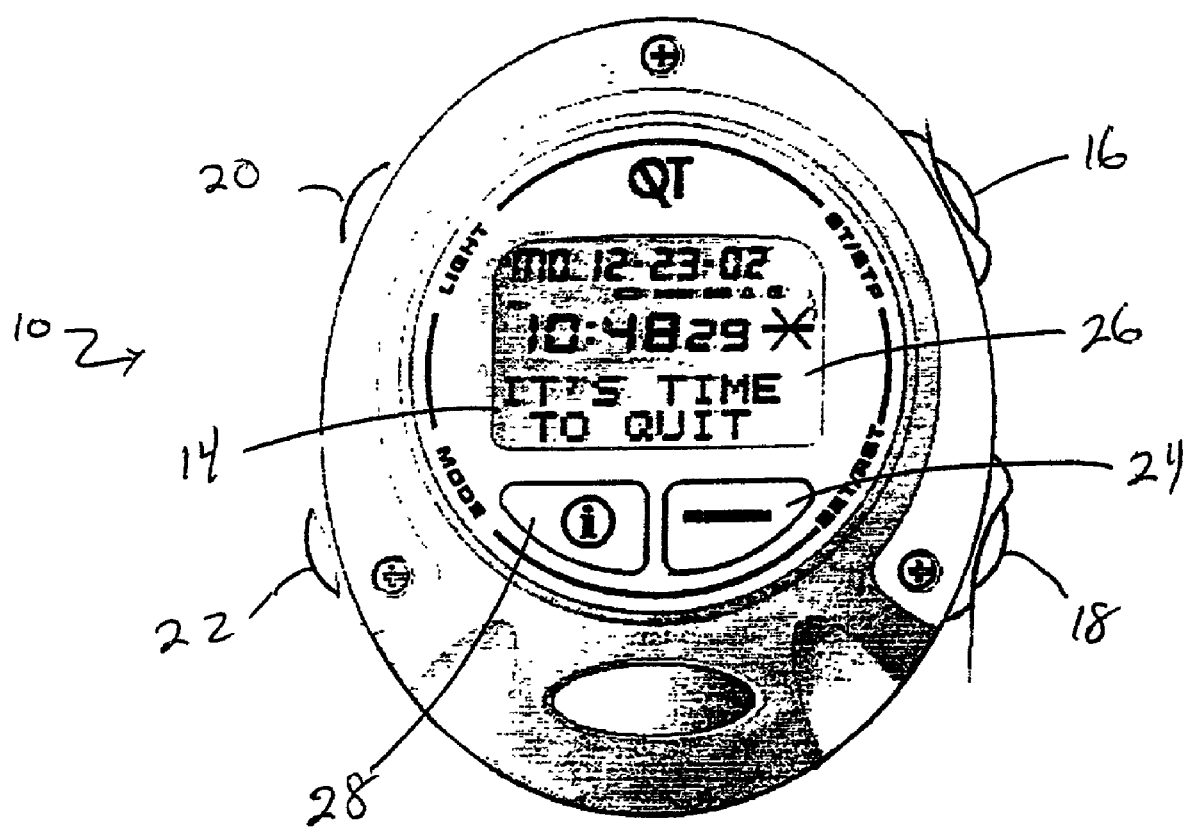
FIG. 1 is a perspective view of the smoking cessation aide in accordance with a preferred embodiment of the present invention.

In accordance with the preferred embodiment of the present invention and as shown in FIG. 1, the invention takes the form of a watch 10. Watch 10 can be attached to a wristband for wearing in a similar fashion as other wristwatches, or attached to a solid or flexible chain similar to a key chain fob, or simply as a watch device. Display 12 can show multiple lines of text 14, and may be of the LED, LCD, or other appropriate construction, and is shown with two lines of display in addition to the lines indicating standard watch display functions such as time, day, etc. In the illustrated form, there are five input buttons: four are on the side of the watch 16, 18, 20, and 22, and one on the clock face, having a symbol indicative of a cigarette 24. Normally, the watch may display the time, date, and a cigarette message in display 12. The message may change, for example, every 20 seconds. It may display in sequence the total number of cigarettes of the day, the time since the user smoked the most recent cigarette, a supportive message, a combination thereof, or any other appropriate display. The aide may be programmed so that, for example, every 10 minutes throughout the day, the watch will display different encouraging messages to help decrease the desire to smoke. These messages may be customized to be more encouraging with a fast rate of decline of smoking or more empathetic if the rate is slow. When no cigarettes have been smoked, for example, the watch may be programmed to display the number of days of abstinence and a different congratulatory message about the achievement or the health benefits. In addition, there is a cigarette rate monitor 26 displayed in the display 12 near the time display that is displayed in sections over time to encourage a user to avoid beginning the habit, in this case smoking, at least until the entire displayed is complete.

Figure 2:
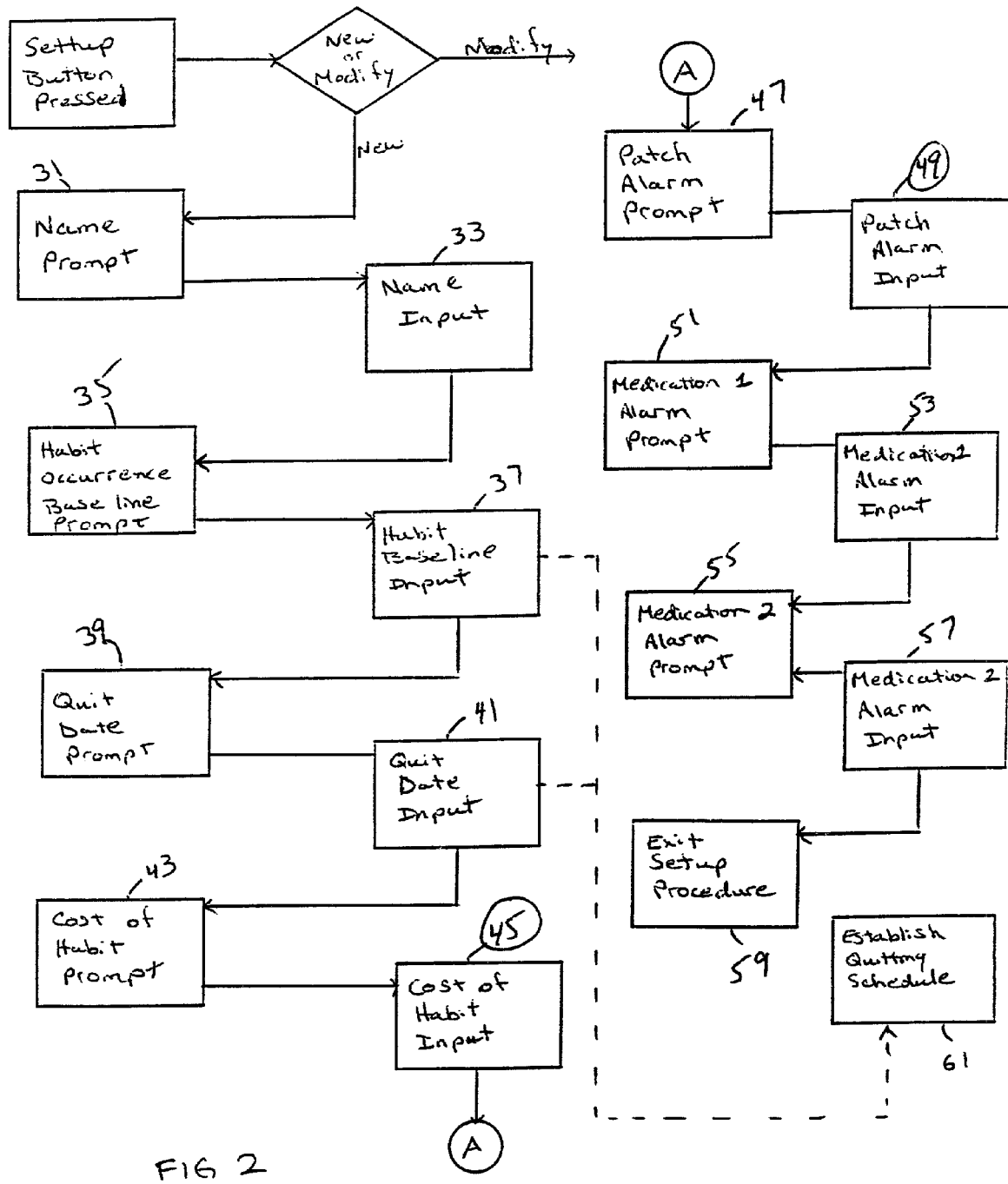
FIG. 2 is a flow diagram of the Setup procedure of the program of the illustrated embodiment of the present invention.

In operation, the user begins the quitting process by setting the quitting schedule and inputting other basic information at the setup process as in FIG. 2. Though the particular button may be varied, in the illustrated embodiment, the lower right button is designated the Setup button 18. Upon hitting Setup button 18, the user is lead step-by-step through inputting the required information. Though not necessarily the only information, or the needed information, in the particular embodiment shown, the user during the setup process selects that the user is either establishing a new quitting schedule or modifying a previously entered schedule. The user may select either new or modify by the remaining buttons in any of a variety of well established ways such as toggling between the two options by pressing the buttons. In the illustrated form, the user selects whether the schedule is a new schedule or the modification of a prior schedule by use of buttons 16 and 20. The setup of a new schedule will be explained in detail below, though it will be appreciated that modifying a previously input schedule may be performed in a similar fashion.

Upon selecting that the quitting schedule is a new schedule, the user is prompted to input the user's name 31. In the preferred embodiment, a letter will appear on the display 12 and by pressing buttons 16, 20, the letter will advance or retreat by one letter in the order of the alphabet, and may include capital letters, small letters, and symbols. To indicate completion of the name input 33, the user may, for example press button 22, or setup button 18 again, depending upon programming preference. The user is then prompted to input the baseline number of times the habit occurs in the appropriate time period 35. In the illustrated embodiment, the habit is smoking a cigarette and the time period is one day. Display 12 may be preset to show a particular number, such as 20, and the user may increase or decrease that number by pressing, for example buttons 16, 20 in a similar fashion as the user changed the displayed letter during input of the user's name. Upon the number of times the user smokes a cigarette in a day is displayed 37, the user indicates completion in a similar fashion as the input name, for example pressing button 22 or 18.

The user is then prompted to input the date by which they desire to quite the habit 39, in this case cigarette smoking. Display 12 may be preprogrammed to show the date equal to the number of day the user input as the number of cigarettes smoked in a day in the previous step. The termination date may be advanced or retreated by the user in a similar fashion as described above, for example by pressing buttons 16, 20. Upon display of the desired quitting date 41, the user indicates completion in a similar fashion to that described above, for example by pressing buttons 22 or 18. In an alternate embodiment, the user may select the number of days desired to quit without correlating that number of days to a particular calendar date. The number of days may be displayed and altered as described above. In an alternate embodiment, the program may select a termination date without input or modification by the user based upon the baseline number of times the habit occurs.

In the preferred embodiment, the user is next prompted to input the cost of a package of cigarettes 43. Because the device may be used with a variety of habits and over a long period of time, the cost is variable. Display 12 may be preset to show a cost of, for example $4.00 and may be increased and decreased by a set amount, $0.10 for example, each time buttons 16, 20 are pressed 45. Though this information is not necessary for the operation of the invention, it is included as a desired feature, as other features may be included.

Because the preferred use of the present invention is in connection with cigarette smoking, and because currently, many people wanting to stop smoking are applying a nicotine patch or taking other medication(s), the setup feature will then prompt the user if the user wants to activate the patch alarm for the purpose of setting an alarm, auditory or otherwise, as a reminder to the user to apply a nicotine patch 47. Display 12 may be set to show the word 'yes' or the word 'no' and may then be toggled between the two words by use of buttons 16, 20 in a similar fashion as described above. Alternately, both words may appear and one highlighted. The user may toggle between highlighting one or the other words by pressing buttons 16, 20. If the user selects that they want to use the patch alarm function, the user is then prompted to input the time the user wants the alarm to go off. Similar to that described above, display 12 may be set to show for example 8:00 am and that time may be advanced or retreated by pressing buttons 16, 20 as described above an input selection is completed 49. If the user selects that they do not want to use the patch alarm function 49, the setup feature then prompts the user if the user wants to activate a medication alarm 51, 55, of which there are two because it is often the case that a person wanting to quit cigarette smoking may take medication twice each day. Similar to that described above in connection with the patch alarm, the user may decide to use or not use each medication alarm. Display 12 may be set to display a particular time form each medication alarm desired and may be modified by the user in accordance with the above described patch alarm feature. In the preferred embodiment, medication alarm 1 is preset to 9:00 am and medication alarm 2 is preset at 6:00 pm, but each may be modified by the user 53, 57 and described above.

At the user-set time, if the user sets the patch alarm, patch alarm will go off and a message may be displayed in display 12 such as 'time to apply patch' or 'put your patch on'. Similarly, at the user-set time, if the user sets medication alarm 1 or medication alarm 2, medication alarm 1 and medication alarm 2 will go off and a message may be displayed in display 12 such as 'time to take medication' or 'take your medication'.

Though the above information is prompted for input by the user in the preferred embodiment, any information may be used as is appropriate for a particular habit. Upon entering all information in the setup procedure, the setup procedure is terminated 59 either automatically or by the pressing of a button.

With the above input information, particularly the habit occurrence baseline 37 and the quitting date 41, the programming of watch 10 determines a quitting schedule 61, as is shown in dotted lines at FIG. 2. As is appreciated, because the user sets the habit termination date, the user thereby also sets the quitting schedule. In the illustrated embodiment, the programming will calculate the number of cigarettes the user should smoke each time period, for example a day, beginning with the first day being the number of cigarettes the user input as the number of cigarettes normally smoked in a day and decreasing the number of cigarettes appropriately until the termination date is reached having a target number of cigarettes for that day of zero cigarettes. The schedule may be of any appropriate format such as linearly, more heavily weighted towards the beginning of the quitting schedule, more weighted towards the end of the schedule, more weighted towards the middle of the schedule, more weighted toward the beginning and end of the schedule, or any other scheme appropriate for the habit and circumstances.

An overall visual indication of the degree to which the user is on track with the user-set quitting schedule is established. In the preferred embodiment, the overall indication is by a number and that number is initially set at 85, though other visual indication may be used. For example, a different number, a movable gauge, or fillable diagram or symbol may be a suitable visual indication. The number 85 is selected in the preferred embodiment, as many people are familiar with the percentage indicator of between 0% and 100%, where 60% indicates failure and 100% indicates complete success, such as in may school exam situations. Accordingly, the number 85 is first set, indicating to many users a middle 'B' grade or 85% success. The visual indicator will then be adjusted up or down depending upon the user's ability to maintain the user-set quitting schedule as described in more detail below.

After each time watch 10 detects the passing of 12:00 midnight, the program will reset the number of times the habit occurs to zero for the following 24 hour time period. The user must indicate the beginning of a new day by, in the illustrated embodiment, pressing information button 28, or pressing information button 28 twice in succession, for example. If the user does not use watch 10 during a 24 hour period, the overall visual indicator of success is lowered by a determined amount, for example 1. If the user does not use the watch for 2 days in a row, watch 10 may be programmed to set off the alarm several times during the day, such as for example 12:00 noon and 6:00 pm.

Figure 3:
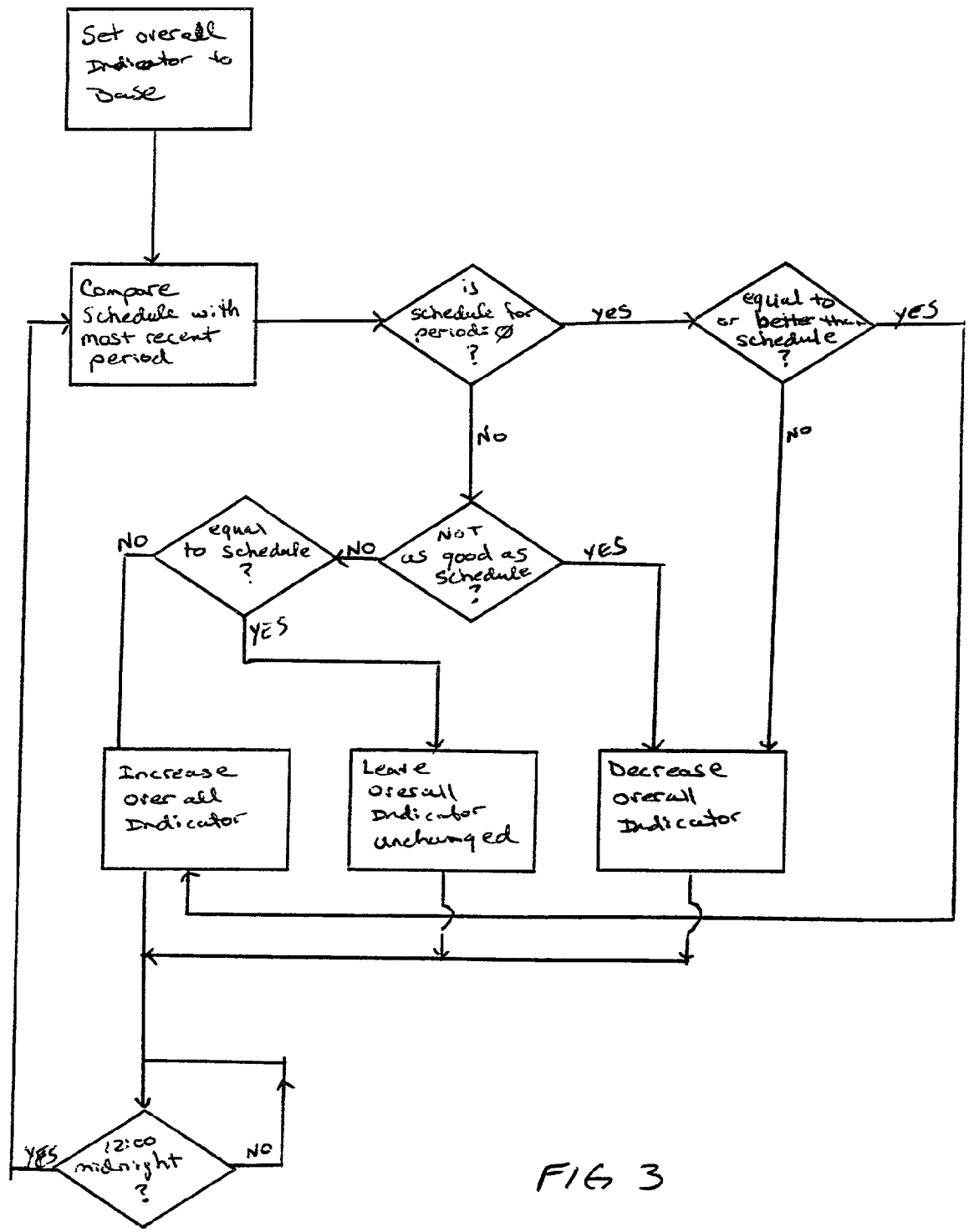
FIG. 3 is a flow diagram of procedure to modify the overall visual indicator of the program.

Each time the user begins the habit, lights up a cigarette to smoke for example, the user is to indicate such by pressing cigarette button 24. The programming inside watch 10 keeps track of the times cigarette button 24 is presses and upon reaching 12:00 midnight compares the total number for that day to the user-set quitting schedule for that day and determines if modification of the overall visual indicator is needed as is shown in one example in FIG. 3. If the total number of cigarettes smoked in a day is equal to the number of cigarettes indicated by the user-set schedule the overall visual indicator remains unchanged. If, however, the user smokes more that the user-set schedule indicates, the overall visual indicator is decreased by, for example, 1. If the number of cigarettes smokes is less than the number of cigarettes indicated by the user-set schedule, the overall visual indicator is increased by 1, for example. As is appreciated, over a 15 day period, the overall visual indicator may be increased to 100, decreased to 70, or may fluctuate between. In the event the number of cigarettes smoked in a day is zero and that is the same number indicated by the user-set schedule, the overall visual indicator may be increased by, for example, 1, so that the user understands that not smoking, even if according to the user-set schedule, is an improvement. The number of times cigarette button 24 is pressed is retained in memory and at 12:00 midnight is compared to the user-set schedule to increase, decrease, or leave unchanged the visual indicator. The first day is set at the baseline, in this case 85.

In the preferred embodiment, if the overall visual indicator gets below a predetermined amount, such as 60 in the illustrated embodiment, watch 10 may be preprogrammed to reset the number to 70 and recalculate a preset number of days before termination, recalculating the termination date and quitting schedule. This feature is to avoid the user having a feeling of failure and wanting to give up trying to quit smoking. The number of days to termination may be preset, or may be based on the number of days set by the user during the setup process.

Information button is position in the illustrated embodiment near cigarette button 24. Accordingly, the user may choose to press information button 28 rather than lighting a cigarette and pressing cigarette button 24 thereby delaying smoking a cigarette for an amount time. Upon pressing information button 28 and holding information button 18 down for a preset period of time, display 12 will, in succession, display first the number of times cigarette button 24 was pressed so far that day, e.g. 'today 3', and the number of cigarettes targeted to be smoked that day to comply with the user-set quitting schedule, e.g. 'goal 8', next display the time and date cigarette button 24 was most recently pressed, next display the elapsed time since cigarette button 18 was most recently pressed and will automatically indicate the amount of time in minutes, hours/minutes, or days/hours, depending upon the amount of time elapsed, next display the overall visual indication of the degree to which the user is keeping to the user-set quitting schedule, and lastly display the amount of money saved when compared to the amount of money that would have been spent on cigarettes had the user continued smoking at the rate input during the setup procedure.

Upon pressing information button 28 for a shorter predetermined amount of time, display 12 in the preferred embodiment will display a message. Such message can be of an encouraging nature, a reinforcing nature, a factual nature, or otherwise and may be dependent upon the overall visual indication of the degree to which the user is keeping to the user-set quitting schedule. In particular, messages appropriate for a user that has not smoked in several days, i.e., a non-smoker, may be included and displayed when the user has not smoked.

Display 12 may also show short textual messages that change regularly. The messages may be of any appropriate nature and in the preferred embodiment fit within two lines of ten characters each. The messages can be dependent upon the overall visual indication of the success degree, and may also be in comparison to the user-set quitting schedule and the number of times cigarette button 24 was pressed so far in that 24 hour time period.

It will be appreciated that the information input during the setup process can be incorporated in the messages shown in display 12, such as the user's name and cost information.

The alarm may also go off at times other than the patch alarm time and medication alarm time. For example, it may go off a short time after the user presses cigarette button 24 signaling the user to put the cigarette out early. The alarm can be programmed to not occur all of the time, or at random intervals after initiating lighting a cigarette. For example, the alarm will occur 30% of the time when less then 10 cigarettes are smoked and increase in frequency as more cigarettes are smoked in a day. In an alternate embodiment, the user can set the alarm to be vibratory, auditory, both, or random. The programming required to perform these tasks is enclosed inside watch 10 and is within the skill of those of ordinary skill.

The device can also be used as an alarm clock, timer or chronograph, and uses a standard watch battery, or other suitable battery, for power, as many wristwatches and handheld devices on the market, incorporated herein by reference. A wrist strap may be adjustable for standard wrist sizes and the watch may come in different colors and materials.

In the illustrated embodiment, display 12 includes at least three sub-displays: the current time and date, the message display, and the rate monitor display. The current time and date display are self-explanatory and display the current time and date as is customary in many displays. The message display has been described in more detail above and may display current smoking frequency statistics or display encouraging, factual, or other messages.

Rate monitor display 26 provides a continual graphical representation of the current time since the last cigarette has been smoked. In the preferred embodiment, rate monitor 26 is a sectioned cigarette with an 'X' therethrough whose total image represents the time between cigarettes needed to decrease the current average amount of cigarettes consumed each day by the user-set schedule. For example, as the user decreases their rate of smoking, the sectioned cigarette image represents a longer period of time to encourage the user to continue to decrease their rate of smoking. At a selected interval, approximately 5–10 minutes, for example, after the cigarette button has been pressed, the rate monitor 26 resets and the process repeats.

While the invention has been described in connection with a preferred embodiment, it is not intended to limit the scope of the invention to the particular form set forth, but on the contrary, it is intended to cover such alternatives, modifications, and equivalents as may be included within the spirit and scope of the invention as defined by the appended claims.

The invention claimed is:

1. A habit cessation aide comprising:
   a user-modifiable quitting schedule based on the date, or number of days, to quit the habit and user input of at least a baseline number of times the habit occurs in a given time period,
   a user-initiated habit-occurrence indicator,
   a display for displaying messages dependent upon the quitting schedule and the number of times the user-initiated habit-occurrence indicator is used, such messages not to include a message that the habit can or should be performed, and
   an overall visual indication of the degree to which the user is maintaining the quitting schedule based upon the quitting schedule and the number of times the user-initiated habit-occurrence indicator is used.

2. A habit cessation aide as claimed in claim 1 wherein the habit is smoking.

3. A habit cessation aide as claimed in claim 1 further comprising an alarm.

4. A habit cessation aide as claimed in claim 3 wherein the alarm can also be used to indicate a message selected from the group consisting of time to apply nicotine patch and time to take medication.

5. A habit cessation aide as claimed in claim 1 wherein the aide is in the form of a wristwatch.

6. A habit cessation aide as claimed in claim 1 wherein the date, or number of days, to quit the habit is input by the user.

* * * * *